United States Patent
Nuno et al.

(10) Patent No.: US 12,059,505 B2
(45) Date of Patent: Aug. 13, 2024

(54) AIR CONDITIONER

(71) Applicant: DAIKIN INDUSTRIES, LTD., Osaka (JP)

(72) Inventors: Hayato Nuno, Osaka (JP); Hiroshi Itou, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 369 days.

(21) Appl. No.: 17/706,072

(22) Filed: Mar. 28, 2022

(65) Prior Publication Data
US 2022/0211893 A1 Jul. 7, 2022

Related U.S. Application Data

(63) Continuation of application No. PCT/JP2020/034254, filed on Sep. 10, 2020.

(30) Foreign Application Priority Data

Sep. 30, 2019 (JP) .................. 2019-178349

(51) Int. Cl.
| | |
|---|---|
| A61L 2/10 | (2006.01) |
| A61L 2/24 | (2006.01) |
| F24F 11/30 | (2018.01) |
| F24F 11/70 | (2018.01) |

(52) U.S. Cl.
CPC .............. *A61L 2/24* (2013.01); *A61L 2/10* (2013.01); *F24F 11/30* (2018.01); *F24F 11/70* (2018.01); *A61L 2202/14* (2013.01)

(58) Field of Classification Search
CPC .......... A61L 2/24; A61L 2/10; A61L 2202/14; F24F 11/30; F24F 11/70; F24F 11/74; F24F 13/222; F24F 2140/20; F24F 1/0071; F24F 8/22; F24F 2110/10; Y02B 30/70
USPC ..................................... 250/455.11
See application file for complete search history.

(56) References Cited

U.S. PATENT DOCUMENTS

| | | | |
|---|---|---|---|
| 2015/0283279 A1* | 10/2015 | Lott .......... | G01F 1/76 250/428 |
| 2018/0110890 A1 | 4/2018 | Matsui | |
| 2018/0373157 A1 | 12/2018 | Kimsey-Lin | |

(Continued)

FOREIGN PATENT DOCUMENTS

| | | |
|---|---|---|
| CN | 109771678 A | 5/2019 |
| JP | 2000-111076 A | 4/2000 |
| JP | 2004-232944 A | 8/2004 |

(Continued)

OTHER PUBLICATIONS

International Search Report for PCT/JP2020/034254 mailed on Oct. 27, 2020.

(Continued)

*Primary Examiner* — Kiet T Nguyen
(74) *Attorney, Agent, or Firm* — Birch, Stewart, Kolasch & Birch, LLP

(57) ABSTRACT

Provided is an air conditioner including an irradiation unit that irradiates an irradiation area of an indoor unit with ultraviolet rays, a temperature detection unit that detects an ambient temperature of the irradiation unit, and a control unit that controls an irradiation time of the irradiation unit. The control unit controls the irradiation time in accordance with the ambient temperature detected by the temperature detection unit.

6 Claims, 5 Drawing Sheets

(56) References Cited

U.S. PATENT DOCUMENTS

2019/0262493 A1   8/2019   Collins et al.

FOREIGN PATENT DOCUMENTS

JP        2005-95400 A     4/2005
JP        2017-133700 A    8/2017

OTHER PUBLICATIONS

Written Opinion of the International Searching Authority for PCT/JP2020/034254 mailed on Oct. 27, 2020.
International Preliminary Report on Patentability and English translation of the Written Opinion of the International Searching Authority for International Application No. PCT/JP2020/034254, dated Apr. 14, 2022.
Extended European Search Report for European Application No. 20870790.1, dated Sep. 21, 2022.

\* cited by examiner

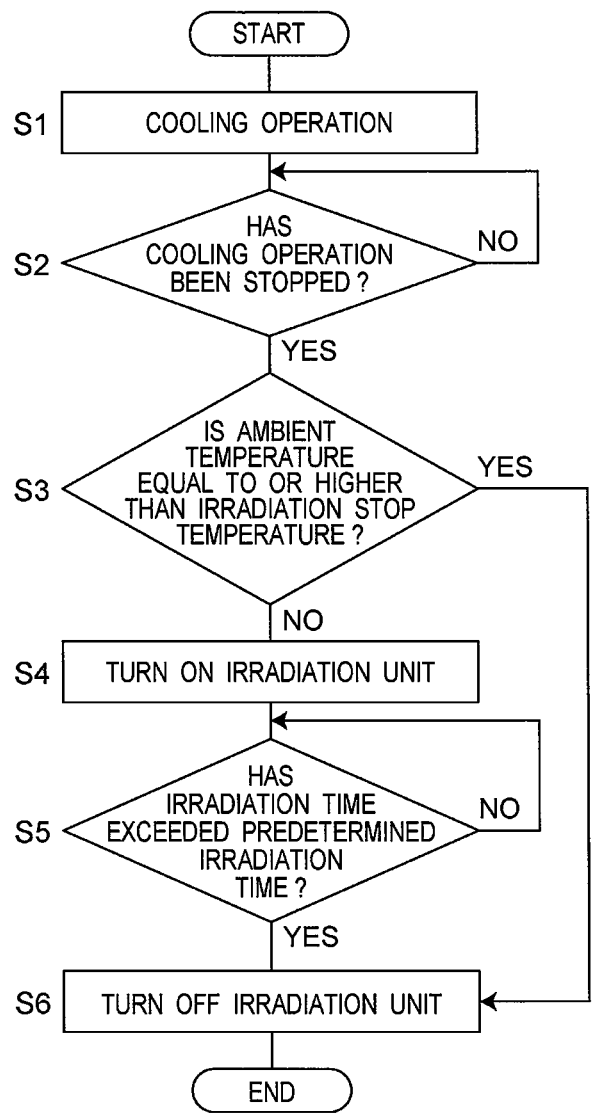

AIR CONDITIONER

CROSS REFERENCE TO RELATED APPLICATIONS

This application is a Continuation of PCT International Application No. PCT/JP2020/034254, filed on Sep. 10, 2020, which claims priority under 35 U.S.C. 119(a) to Patent Application No. 2019-178349, filed in Japan on Sep. 30, 2019, all of which are hereby expressly incorporated by reference into the present application.

TECHNICAL FIELD

The present disclosure relates to air conditioners.

BACKGROUND ART

There is known an air conditioner in which a drain pan where drain water is stored is irradiated with deep ultraviolet rays having a relatively short wavelength among the ultraviolet rays (see, for example, Japanese Laid-Open Patent Publication No. 2017-133700). The irradiation with deep ultraviolet rays causes denaturation or inactivation of bacteria, mold, or the like contained in the drain water (hereinafter, referred to as "sterilization").

SUMMARY

Patent Literature 1 discloses that an irradiating operation is performed in relation to a cooling operation, but does not disclose a relationship between an ambient temperature of an irradiation unit that applies deep ultraviolet rays and an irradiation time of the irradiation unit. Intensity of the deep ultraviolet rays from the irradiation unit, i.e., the illumination intensity of the irradiation unit, varies, depending on the ambient temperature of the irradiation unit. That is, the higher the ambient temperature of the irradiation unit, the lower the illumination intensity of the irradiation unit. This prevents an illumination intensity sufficient for sterilization from being obtained and thus makes the sterilization effect lower.

The present disclosure provides an air conditioner that suppresses a decrease in sterilization effect caused by an ambient temperature of an irradiation unit.

An air conditioner according to an aspect of the present disclosure includes an irradiation unit configured to irradiate an irradiation area of an indoor unit of the air conditioner with ultraviolet rays, a temperature detection unit configured to detect an ambient temperature of the irradiation unit, and a control unit configured to control an irradiation time of the irradiation unit. The control unit controls the irradiation time in accordance with the ambient temperature detected by the temperature detection unit.

BRIEF DESCRIPTION OF THE DRAWINGS

FIG. 6 is a control flowchart of an ultraviolet rays irradiating operation of the air conditioner.

DESCRIPTION OF EMBODIMENTS

Figure 1:
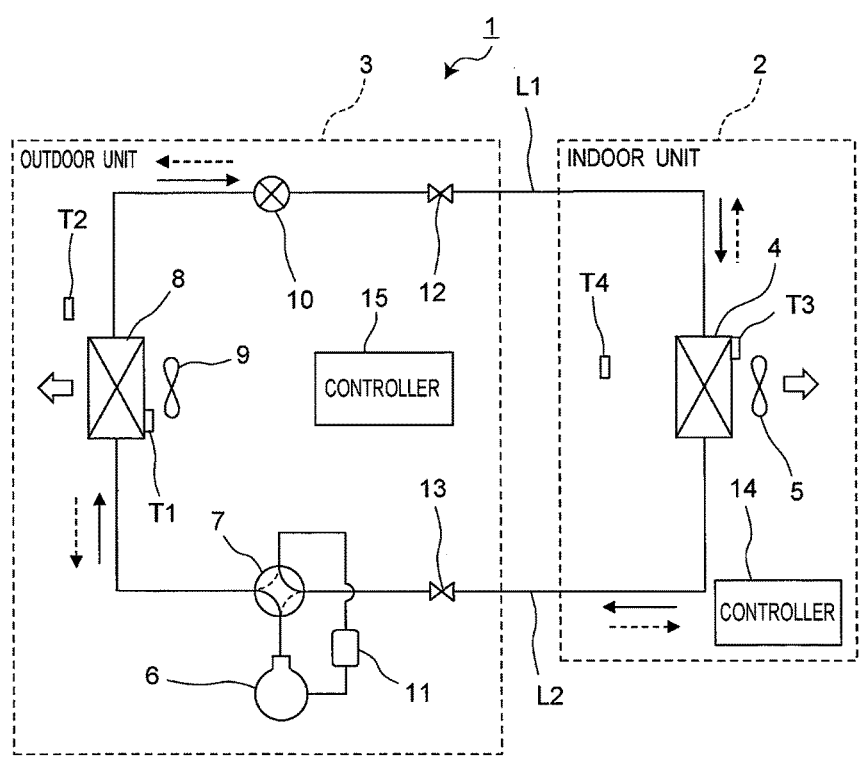
FIG. 1 is a diagram illustrating a refrigerant circuit of an air conditioner according to an embodiment.

Hereinafter, an air conditioner according to an embodiment of the present disclosure will be described with reference to the drawings. Note that the same parts in the drawings are denoted by the same reference sign, and no redundant description will be given.

[Overall Configuration of Air Conditioner 1]

FIG. 1 is a diagram illustrating a refrigerant circuit of an air conditioner 1 according to the embodiment of the present disclosure. As illustrated in FIG. 1, the air conditioner 1 includes an indoor unit 2 installed indoors and an outdoor unit 3 installed outdoors, the indoor unit 2 and the outdoor unit 3 being connected with each other via connection pipes L1, L2. The air conditioner 1 is of a type in which the indoor unit 2 is paired one-to-one with the outdoor unit 3.

The indoor unit 2 is equipped with an indoor heat exchanger 4 and an indoor fan 5. The outdoor unit 3 is equipped with a compressor 6, a four-way switching valve 7, an outdoor heat exchanger 8, an outdoor fan 9, an electric expansion valve (hereinafter, referred to as an expansion valve) 10 as an example of the decompressing mechanism, and an accumulator 11. The outdoor unit 3 is further provided with a liquid-side shutoff valve 12 and a gas-side shutoff valve 13.

The compressor 6, the four-way switching valve 7, the outdoor heat exchanger 8, the expansion valve 10, the indoor heat exchanger 4, the accumulator 11, and the compressor 6 are connected in this order via a refrigerant pipe and the connection pipes L1, L2 to form a refrigerant circuit. The liquid-side shutoff valve 12 is interposed between the expansion valve 10 and the connection pipe L1, and the gas-side shutoff valve 13 is interposed between the four-way switching valve 7 and the connection pipe L2.

In the refrigerant circuit, the compressor 6 has a discharge port connected to the outdoor heat exchanger 8 via the four-way switching valve 7 and has an intake port connected to the indoor heat exchanger 4 via the four-way switching valve 7 and the accumulator 11.

A remote controller 17 (hereinafter, referred to as a "remote control 17") can bring the air conditioner 1 configured as described above into cooling operation, dehumidifying operation, and heating operation. The remote control 17 can switch, start, or stop various operations, set an indoor temperature, set a rotational speed of the indoor fan 5, and the like.

During the cooling operation and the dehumidifying operation, a cooling cycle is established as indicated by solid arrows in which a refrigerant discharged from the compressor 6 sequentially flows from the four-way switching valve 7 to the indoor heat exchanger 4 through the outdoor heat exchanger 8 and the expansion valve 10 and returns to the compressor 6 through the four-way switching valve 7 and the accumulator 11. That is, the outdoor heat exchanger 8 functions as a condenser, and the indoor heat exchanger 4 functions as an evaporator. Note that, during the dehumidifying operation, although the indoor fan 5 is driven to an extent less than during the cooling operation, the refrigerant passing through the indoor heat exchanger 4 evaporates as a result of exchanging heat with indoor air. This causes moisture in the air to be condensed and collected on a surface of the indoor heat exchanger 4, thereby dehumidifying the air inside the room. Therefore, an operation during which condensed water is generated on the surface of the indoor heat exchanger 4 such as the cooling operation and the dehumidifying operation is herein referred to as a cooling operation.

On the other hand, during the heating operation, a heating cycle is established as indicated by dashed arrows in which the four-way switching valve 7 is switched to cause the refrigerant discharged from the compressor 6 to sequentially flow from the four-way switching valve 7 to the outdoor heat exchanger 8 through the indoor heat exchanger 4 and the expansion valve 10 and return to the compressor 6 through the four-way switching valve 7 and the accumulator 11. That is, the indoor heat exchanger 4 functions as a condenser, and the outdoor heat exchanger 8 functions as an evaporator.

As illustrated in FIG. 1, the indoor unit 2 is equipped with an indoor-unit controller (control unit) 14 that controls various operations of the indoor unit 2, and the outdoor unit 3 is equipped with an outdoor-unit controller (control unit) 15 that controls various operations of the outdoor unit 3. The air conditioner 1 is controlled as a whole by the indoor-unit controller (control unit) 14 or the outdoor-unit controller (control unit) 15, or under cooperation between the indoor-unit controller (control unit) 14 and the outdoor-unit controller (control unit) 15. Therefore, at least either the indoor-unit controller 14 or the outdoor-unit controller 15 acts as a control unit 16 that controls various operations of the air conditioner 1.

Figure 2:
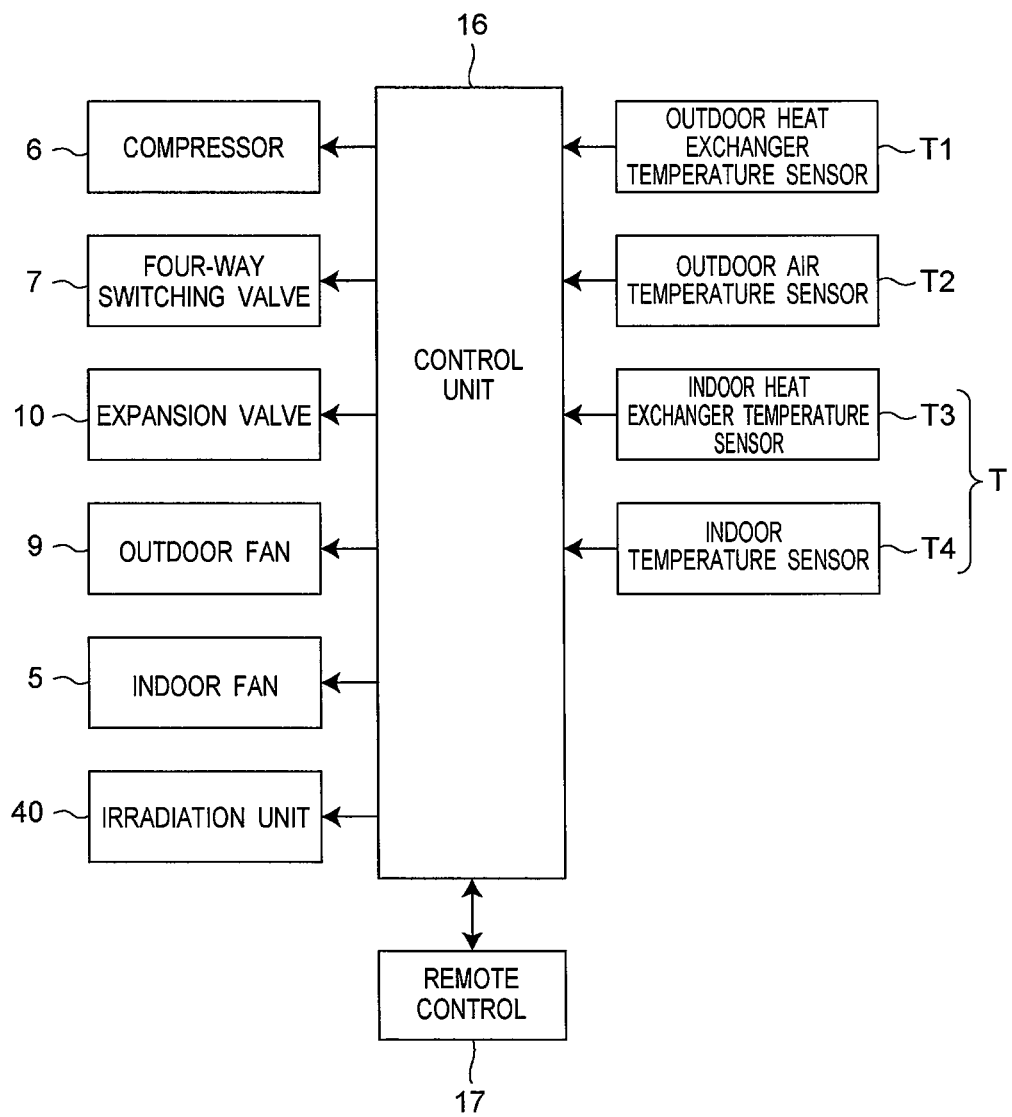
FIG. 2 is a control block diagram of the air conditioner illustrated in FIG. 1.

As illustrated in FIG. 2, the compressor 6, the four-way switching valve 7, the expansion valve 10, the indoor fan 5, and the outdoor fan 9 are connected to the control unit 16. Specifically, various drive units (e.g., a motor and a solenoid) for driving such components are connected to the control unit 16. An outdoor heat exchanger temperature sensor T1, an outdoor air temperature sensor T2, an indoor heat exchanger temperature sensor T3, and an indoor temperature sensor T4 are connected to the control unit 16. An irradiation unit 40 is connected to the control unit 16.

The outdoor heat exchanger temperature sensor T1 is installed in the outdoor heat exchanger 8 to detect a temperature of the outdoor heat exchanger 8. The outdoor air temperature sensor T2 is installed in the outdoor unit 3 to detect an outdoor temperature.

The indoor heat exchanger temperature sensor T3 is installed in the indoor heat exchanger 4 to detect a temperature of the indoor heat exchanger 4. Therefore, the indoor heat exchanger temperature sensor T3 acts as a first sensor that detects the temperature of the indoor heat exchanger 4.

The indoor temperature sensor T4 is installed near an indoor air intake port of the indoor unit 2. The indoor temperature sensor T4 detects a temperature of indoor air flowing into the indoor unit 2 (that is, the indoor temperature). Therefore, the indoor temperature sensor T4 acts as a second sensor that detects the indoor temperature. The indoor heat exchanger temperature sensor T3 and the indoor temperature sensor T4 are both thermistors.

A temperature detection unit T configured to detect the ambient temperature of the irradiation unit 40 includes the indoor heat exchanger temperature sensor T3 and the indoor temperature sensor T4. The use of the sensors (the indoor heat exchanger temperature sensor T3 and the indoor temperature sensor T4) already existing in the air conditioner 1 for the temperature detection unit T eliminates the need of installing an additional sensor and thus can reduce both the number of components and cost. The ambient temperature of the irradiation unit 40 is obtained as a weighted average of the temperature of the indoor heat exchanger 4 detected by the indoor heat exchanger temperature sensor T3 and the indoor temperature detected by the indoor temperature sensor T4. Note that, when another temperature sensor such as a thermistor is installed near the irradiation unit 40, the ambient temperature of the irradiation unit 40 can be detected in the immediate proximity of the irradiation unit 40.

The control unit 16 includes a microcomputer, an input-output circuit, and the like. The control unit 16 controls the operation of the air conditioner 1 by performing operation processing, determination processing, or the like based on a command (such as an operation start command or an indoor temperature setting command) sent from the remote control 17 or various temperatures detected by the outdoor heat exchanger temperature sensor T1, the outdoor air temperature sensor T2, the indoor heat exchanger temperature sensor T3, and the indoor temperature sensor T4.

[Configuration of Indoor Unit]

Figure 3:
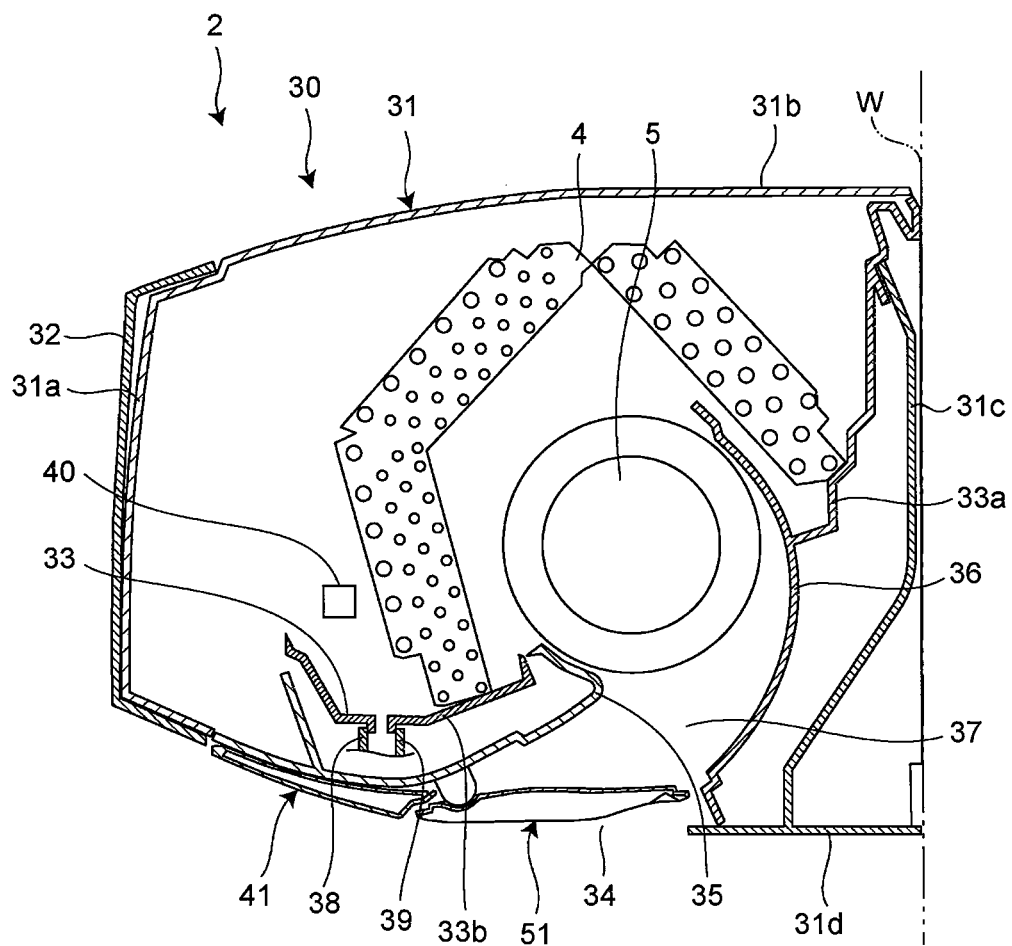
FIG. 3 is a schematic cross-sectional view of an indoor unit that is out of operation, the indoor unit being a component of the air conditioner illustrated in FIG. 1.

FIG. 3 is a schematic cross-sectional view of the indoor unit 2 that is out of operation, the indoor unit 2 being a component of the air conditioner 1. The indoor unit 2 illustrated in FIG. 3 is of a wall-mounted type.

The indoor unit 2 includes a casing 30 including a casing body 31 and a front panel 32. The casing 30 is attached to a wall surface W facing an indoor space and accommodates the indoor fan 5, the indoor heat exchanger 4, the drain pan 33, and the like.

The casing body 31 includes a plurality of parts: a front part 31a, an upper part 31b, a rear part 31c, and a lower part 31d. The front panel 32 is attached to the front part 31a in an openable and closable manner. Further, an intake port (not illustrated) is provided extending from the front part 31a to the upper part 31b.

The front panel 32 is associated with the front part 31a of the indoor unit 2 and has, for example, a flat shape with no intake port. Further, an upper end of the front panel 32 is pivotably supported by the upper part 31b of the casing body 31 and thus can swing in a hinged manner.

The indoor fan 5 and the indoor heat exchanger 4 are attached to the casing body 31. The indoor heat exchanger 4 exchanges heat with indoor air drawn into the casing 30 through the intake port. Further, the indoor heat exchanger 4 has an inverted V shape in a side view with both ends extending downward and a bend positioned higher. The indoor heat exchanger 4 includes a plurality of heat transfer tubes and a large number of fins.

The indoor fan 5 is positioned below the bend of the indoor heat exchanger 4. The indoor fan 5 is, for example, a cross-flow fan. The indoor fan 5 forces indoor air passing through the indoor heat exchanger 4 to flow to a blow-out port 34 of the lower part 31d of the casing body 31.

The casing body 31 is further provided with a first partition wall 35 and a second partition wall 36. A space between the first partition wall 35 and the second partition wall 36 serves as a blow-out flow path 37 through which the indoor fan 5 and the blow-out port 34 communicate with each other.

The drain pan 33 is disposed below the indoor heat exchanger 4 and receives condensed water generated by condensation on the indoor heat exchanger 4. The drain pan 33 includes an upper receiver 33a, a lower receiver 33b, and a connecting part (not illustrated) through which the upper receiver 33a and the lower receiver 33b are connected with each other. The condensed water drops from the indoor heat exchanger 4 into both the upper receiver 33a and the lower receiver 33b. The condensed water dropped into the upper receiver 33a flows down to the lower receiver 33b through the connecting portion. The condensed water flowing down from the upper receiver 33a to the lower receiver 33b and the condensed water dropped into the lower receiver 33b accumulate in the lower receiver 33b as drain water. The drain water accumulated in the lower receiver 33b is drained, by its own weight, outside from a drain port 38 provided in the lower receiver 33b through a drain hose 39. That is, the drain pan 33 is structured to cause the drain water to flow out by its own weight.

The control unit 16 controls the cooling operation to make the temperature of the indoor heat exchanger 4 measured by the indoor heat exchanger temperature sensor T3 lower than the dew point, thereby generating drain water. The control unit 16 can estimate a water level of the drain water accumulated in the lower receiver 33b of the drain pan 33 based on the operation status of the cooling operation. Therefore, the control unit 16 functions as a detection unit that detects the water level of the drain water accumulated in the drain pan 33. Some air conditioners, e.g., air conditioners installed at high places such as ceiling-embedded air conditioners and ceiling-suspended air conditioners, may have a water level sensor installed as a detection unit that detects the water level of the drain water accumulated in the drain pan 33.

The irradiation unit 40 is provided above the drain pan 33. The irradiation unit 40 emits deep ultraviolet rays (hereinafter, referred to as "ultraviolet rays") having a relatively short wavelength among ultraviolet rays to irradiate an upper surface of the drain pan 33 with the ultraviolet rays. The irradiation unit 40 is, for example, an ultraviolet LED (light emitting diode). The ultraviolet rays emitted by the irradiation unit 40 have a wavelength of, for example, 255 nm to 350 nm.

In order to denature or inactivate bacteria, mold, or the like contained in the drain water, i.e., to perform sterilization, it is necessary to emit the ultraviolet rays by a predetermined dose. The dose of the ultraviolet rays to be emitted is determined by multiplying the ultraviolet intensity by the irradiation time, that is, by the ultraviolet intensity * the irradiation time. The control unit 16 controls the ultraviolet intensity and the irradiation time of the irradiation unit 40 so as to obtain the predetermined dose necessary for sterilization.

During the ultraviolet rays irradiating operation, after the cooling operation or the dehumidifying operation, an irradiation area, i.e. an area to be irradiated where bacteria, mold, or the like easily propagates, such as the indoor heat exchanger 4, the filter 47, or the drain pan 33 is irradiated with the ultraviolet rays by the predetermined dose. For example, the irradiation unit 40 irradiates the drain pan 33 with a predetermined dose of ultraviolet rays to sterilize the drain water accumulated in the drain pan 33, thereby allowing the inside of the indoor unit 2 to be kept clean.

The indoor unit 2 includes a first horizontal flap 41 and a second horizontal flap 51 disposed behind the first horizontal flap 41 (adjacent to the wall surface W). The first horizontal flap 41 and the second horizontal flap 51 adjust a vertical direction of air blowing out from the blow-out port 34 (air flowing through the blow-out flow path 37). The first horizontal flap 41 is pivotably attached to the lower part 31d of the casing body 31. In the state illustrated in FIG. 3, the indoor fan 5 is stopped, the front panel 32, the first horizontal flap 41, and the second horizontal flap 51 are closed, and the air conditioning operation by the indoor unit 2 is stopped. Note that the first horizontal flap 41 is an example of a first horizontal blade. Further, the second horizontal flap 51 is an example of a second horizontal blade.

The indoor unit 2 further includes a plurality of vertical flaps (not illustrated) that adjust a lateral direction of air blowing out. The plurality of vertical flaps are arranged in the blow-out flow path 37 at predetermined intervals in a longitudinal direction of the blow-out port 34 (a direction perpendicular to the drawing sheet of FIG. 3). Note that the vertical flap is an example of a perpendicular blade.

[Ultraviolet Rays Irradiating Operation]

Figure 4:
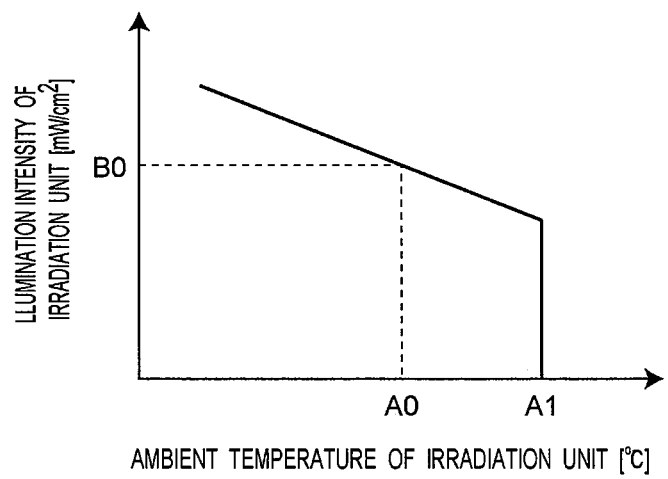
FIG. 4 is a diagram for describing a relationship between an ambient temperature and illumination intensity of an irradiation unit.
Figure 5:
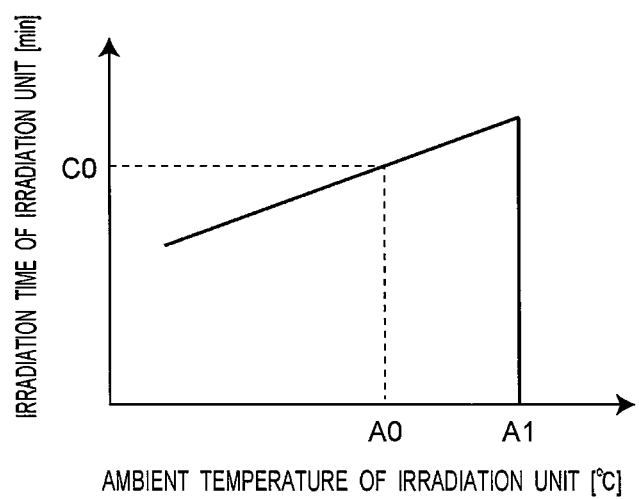
FIG. 5 is a diagram for describing a relationship between the ambient temperature and an irradiation time of the irradiation unit.

Next, the ultraviolet rays irradiating operation of the air conditioner 1 will be described with reference to FIGS. 4 to 6. FIG. 4 is a diagram for describing a relationship between the ambient temperature and the illumination intensity of the irradiation unit 40, FIG. 5 is a diagram for describing a relationship between the ambient temperature and the irradiation time of the irradiation unit 40, and FIG. 6 is a control flowchart of the ultraviolet rays irradiating operation of the air conditioner 1.

[Relationship Between Ambient Temperature and Illumination Intensity of Irradiation Unit]

FIG. 4 schematically illustrates a relationship between the ambient temperature and illumination intensity of the irradiation unit 40. In FIG. 4, the horizontal axis represents the ambient temperature [° C.] of the irradiation unit 40, and the vertical axis represents the illumination intensity [mW/cm$^2$] of the irradiation unit 40. In FIG. 4, A0 denotes a rated ambient temperature when the irradiation unit 40 is placed in operation at the rating, and BO denotes rated illumination intensity corresponding to the rated ambient temperature A0. The rated ambient temperature of the irradiation unit 40 is, for example, 25° C.

As illustrated in FIG. 4, the lower the ambient temperature of the irradiation unit 40, the higher the illumination intensity of the irradiation unit 40, and the higher the ambient temperature of the irradiation unit 40, the lower the illumination intensity of the irradiation unit 40. When the ambient temperature of the irradiation unit 40 becomes equal to or higher than a predetermined irradiation stop temperature A1, the control unit 16 controls the irradiation unit 40 to make the illumination intensity of the irradiation unit 40 equal to zero, that is, to stop the irradiation unit 40 emitting the ultraviolet rays. This can prevent the irradiation unit 40 from being damaged due to an excessive increase in the ambient temperature of the irradiation unit 40. The predetermined irradiation stop temperature A1 of the irradiation unit 40 is, for example, 50° C.

[Relationship Between Ambient Temperature and Irradiation Time of Irradiation Unit]

FIG. 5 schematically illustrates a relationship between the ambient temperature and the irradiation time of the irradiation unit 40. In FIG. 5, the horizontal axis represents the ambient temperature [° C.] of the irradiation unit 40, and the vertical axis represents the irradiation time [min] of the irradiation unit 40. In FIG. 5, A0 denotes a rated ambient temperature when the irradiation unit 40 is placed in operation at the rating, and CO denotes an irradiation time corresponding to the rated ambient temperature A0. The rated ambient temperature of the irradiation unit 40 is, for example, 25° C.

As illustrated in FIG. 5, the lower the ambient temperature of the irradiation unit 40, the shorter the irradiation time of the irradiation unit 40, and the higher the ambient temperature of the irradiation unit 40, the longer the irradiation time of the irradiation unit 40. When the ambient temperature of the irradiation unit 40 becomes equal to or higher than the predetermined irradiation stop temperature A1, the control unit 16 controls the irradiation unit 40 to make the irradiation time of the irradiation unit 40 equal to zero, that is, to stop the irradiation unit 40 emitting the ultraviolet rays. This can prevent the irradiation unit 40 from being damaged due to an excessive increase in the ambient temperature of the irradiation unit 40. The predetermined irradiation stop temperature A1 of the irradiation unit 40 is, for example, 50° C.

[Adjustment to Predetermined Irradiation Time]

A predetermined irradiation time can be adjusted by, for example, the following equation (1):

$$\text{Predetermined irradiation time}=(\text{rated irradiation time})+a*(\text{ambient temperature of irradiation unit}-\text{rated ambient temperature})-b*(\text{rotational speed of indoor fan}) \quad (1)$$

In the equation (1), the rated irradiation time is an irradiation time when the irradiation unit 40 is placed in operation at the rating, and a and b denote predetermined coefficients.

As illustrated in FIG. 5, the higher the ambient temperature of the irradiation unit 40, the longer the predetermined irradiation time of the irradiation unit 40, so that the terms related to the ambient temperature in the equation (1) cause an increase in the predetermined irradiation time.

When the rotational speed of the indoor fan 5 increases, heat around the irradiation unit 40 is further dissipated, and the temperature of the irradiation unit 40 decreases accordingly, so that the term related to the rotational speed of the indoor fan 5 causes a decrease in the predetermined irradiation time.

The predetermined irradiation time is adjusted with the ambient temperature of the irradiation unit 40 and the rotational speed of the indoor fan 5 taken into consideration for the rated irradiation time. Since the predetermined irradiation time of the irradiation unit 40 is adjusted with the ambient temperature of the irradiation unit 40 and the heat dissipation effect of the indoor fan 5 taken into consideration, the irradiation area can be irradiated with the ultraviolet rays with optimum intensity.

[Adjustment to Irradiation Stop Temperature]

The irradiation stop temperature can be adjusted by, for example, the following equation (2):

$$\text{Irradiation stop temperature}=(\text{predetermined irradiation stop temperature})+c*(\text{rotational speed of indoor fan}) \quad (2)$$

In the equation (2), c denotes a predetermined coefficient.

When the rotational speed of the indoor fan 5 increases, heat around the irradiation unit 40 is further dissipated, and the temperature of the irradiation unit 40 decreases accordingly, so that it is possible to increase the irradiation stop temperature. Therefore, the term related to the rotational speed of the indoor fan 5 causes an increase in the irradiation stop temperature. The irradiation stop temperature is adjusted with the rotational speed of the indoor fan 5 into consideration for the predetermined irradiation stop temperature A1. The adjustment to the irradiation stop temperature allows the irradiation by the irradiation unit 40 to be suitably stopped.

[Control of Irradiating Operation]

Next, control of the ultraviolet rays irradiating operation of the air conditioner 1 will be described with reference to FIG. 6. FIG. 6 is a control flowchart of the ultraviolet rays irradiating operation of the air conditioner 1.

In the air conditioner 1, when the cooling operation is selected by operation of the remote control 17 made by the user, the control unit 16 performs the cooling operation desired by the user to place the air conditioner 1 in the cooling operation over a predetermined period of time (step S1).

In step S2, the control unit 16 determines whether the cooling operation has been stopped. When the cooling operation has not been stopped (NO in step S2), the process waits until the cooling operation is stopped. When the cooling operation has been stopped (YES in step S2), the process proceeds to step S3.

In step S3, the control unit 16 determines whether the ambient temperature of the irradiation unit 40 is equal to or higher than the irradiation interrupt temperature. When the ambient temperature of the irradiation unit 40 is equal to or higher than the irradiation interrupt temperature (YES in step S3), the process proceeds to step S6 to turn off the irradiation unit 40. This can prevent the irradiation unit 40 from being damaged due to an excessive increase in the ambient temperature of the irradiation unit 40. When the ambient temperature of the irradiation unit 40 is lower than the irradiation interrupt temperature (NO in step S3), the process proceeds to step S4.

In step S4, the control unit 16 controls the irradiation unit 40 to turn on the irradiation unit 40. Specifically, the control unit 16 applies a rated current and a rated voltage to the irradiation unit 40 to control the irradiation unit 40 so as to cause the irradiation unit 40 to perform irradiation with rated total radiant flux.

In step S5, the control unit 16 determines whether the irradiation time of the irradiation unit 40 exceeds the predetermined irradiation time necessary for sterilization. When the irradiation time is less than the predetermined irradiation time (NO in step S5), the process waits until the predetermined irradiation time elapses. This causes the area to be irradiated where bacteria, mold, or the like easily propagates, e.g., drain water accumulated in the drain pan 33, to be irradiated with the ultraviolet rays for the predetermined irradiation time. This in turn causes the irradiation area to be sterilized and allows the inside of the indoor unit 2 to be kept clean. When the irradiation time exceeds the predetermined irradiation time (YES in step S5), the process proceeds to step S6.

In step S6, the control unit 16 controls the irradiation unit 40 to turn off the irradiation unit 40. When the irradiation unit 40 is turned off, the control of the ultraviolet rays irradiating operation is brought to an end.

In the air conditioner 1, the irradiation time of the irradiation unit 40 is controlled in accordance with the ambient temperature of the irradiation unit 40, so that it is possible to suppress a decrease in sterilization effect caused by the ambient temperature of the irradiation unit 40.

The embodiment of the present disclosure has been described above. However, it should be understood that specific configurations of the present disclosure are not limited to those described in the embodiment. The scope of the present disclosure is indicated by not only the embodiment described above but also the appended claims and further includes equivalents of the claims and all modifications within the scope of the claims.

REFERENCE SIGNS LIST 1 air conditioner
2 indoor unit
3 outdoor unit
4 indoor heat exchanger (heat exchanger)
5 compressor
6 four-way switching valve 7 outdoor heat exchanger (heat exchanger)
8 expansion valve
10 accumulator
11 indoor-unit controller (control unit)
14 outdoor-unit controller (control unit)
15 control unit
16 remote controller (remote control)
30 casing
31 casing body
31a front part
31b upper part
31c rear part
31d lower part
32 front panel
33 drain pan (an irradiation area to be irradiated)
34 blow-out port
35 first partition wall
36 second partition wall
37 blow-out flow path
38 drain port
39 drain hose
40 irradiation unit
41 first horizontal flap
51 second horizontal flap
L1, L2 connection pipe
T temperature detection unit
T1 outdoor heat exchanger temperature sensor
T2 outdoor air temperature sensor
T3 indoor heat exchanger temperature sensor (first sensor)
T4 indoor temperature sensor (second sensor)
W wall surface

What is claimed is:

1. An air conditioner comprising:
an irradiation unit configured to irradiate an irradiation area of an indoor unit of the air conditioner with ultraviolet rays;
a temperature detection unit configured to detect an ambient temperature of the irradiation unit; and
a control unit configured to control an irradiation time of the irradiation unit, wherein
the control unit controls the irradiation time in accordance with the ambient temperature detected by the temperature detection unit.

2. The air conditioner according to claim 1, wherein
the control unit controls the irradiation unit to make the irradiation time longer as the ambient temperature becomes higher and to make the irradiation time shorter as the ambient temperature becomes lower.

3. The air conditioner according to claim 1, further comprising an indoor fan configured to force air subjected to heat exchange by a heat exchanger of the indoor unit to flow into a room, wherein
the control unit controls a rotational speed of the indoor fan, and
the control unit controls the irradiation unit to make the irradiation time shorter as the rotational speed becomes higher and to make the irradiation time longer as the rotational speed becomes lower.

4. The air conditioner according to claim 1, wherein
the control unit controls the irradiation unit to stop irradiation by the irradiation unit when the ambient temperature becomes equal to or higher than an irradiation stop temperature.

5. The air conditioner according to claim 4, further comprising an indoor fan configured to force air subjected to heat exchange by a heat exchanger of the indoor unit to flow into a room, wherein
the control unit controls a rotational speed of the indoor fan, and
the control unit controls the irradiation unit to make the irradiation stop temperature higher as the rotational speed becomes higher.

6. The air conditioner according to claim 1, wherein
the temperature detection unit includes a first sensor that detects a temperature of a heat exchanger of the indoor unit and a second sensor that detects an indoor temperature.

* * * * *